United States Patent
Lee et al.

(10) Patent No.: US 10,018,550 B2
(45) Date of Patent: Jul. 10, 2018

(54) SYSTEM AND METHOD FOR ANALYZING BLOOD CELL

(71) Applicant: NEW OPTICS, LTD., Yangju-si, Gyeonggi-do (KR)

(72) Inventors: Kyu Man Lee, Uijeongbu-si (KR); Tae Ho Jun, Daegu (KR)

(73) Assignee: NEW OPTICS, LTD., Yangiu-si (KR)

( * ) Notice: Subject to any disclaimer, the term of this patent is extended or adjusted under 35 U.S.C. 154(b) by 0 days.

(21) Appl. No.: 15/351,933

(22) Filed: Nov. 15, 2016

(65) Prior Publication Data

US 2018/0128730 A1 May 10, 2018

(30) Foreign Application Priority Data

Nov. 9, 2016 (KR) .................... 10-2016-0148683

(51) Int. Cl.
*G01N 15/14* (2006.01)
*G01N 33/49* (2006.01)

(52) U.S. Cl.
CPC ..... *G01N 15/1434* (2013.01); *G01N 15/1429* (2013.01); *G01N 33/49* (2013.01)

(58) Field of Classification Search
CPC ........................... G01N 33/48; G01N 15/1434
USPC ......................................................... 356/39
See application file for complete search history.

(56) References Cited

U.S. PATENT DOCUMENTS

| | | | |
|---|---|---|---|
| 4,675,300 A * | 6/1987 | Zare ................. | G01N 21/645 204/452 |
| 2010/0220315 A1* | 9/2010 | Morrell ............ | G01N 15/1436 356/73 |
| 2012/0001090 A1* | 1/2012 | Takasaki .......... | G01N 15/1434 250/459.1 |

FOREIGN PATENT DOCUMENTS

| | | |
|---|---|---|
| JP | 2008-292448 A | 12/2008 |
| JP | 2016-057309 A | 4/2016 |
| KR | 10-0619256 B1 | 8/2006 |

* cited by examiner

*Primary Examiner* — Roy M Punnoose
(74) *Attorney, Agent, or Firm* — Novick, Kim & Lee, PLLC; Jae Youn Kim

(57) ABSTRACT

Provided are a system and a method for analyzing a blood cell. The system includes a laser generator installed around a moving path, along which an analysis target blood cell moves, to generate a laser beam; a plurality of photodetectors configured to detect a laser beam generated as a result of refraction, reflection, transmission or fluorescence of the laser beam generated from the laser generator and incident upon the analysis target blood cell; and an optical fiber configured to focus the laser beam generated from the laser generator and to irradiate the focused laser beam to a measurement point existing on the moving path, wherein the optical fiber transfers a laser beam scattered through a blood cell to the photodetectors; and an analysis apparatus configured to analyze the analysis target blood cell by using the laser beam detected by the photodetectors.

11 Claims, 7 Drawing Sheets

SYSTEM AND METHOD FOR ANALYZING BLOOD CELL

BACKGROUND OF THE INVENTION

1. Field of the Invention

The present invention relates to an apparatus and a method for analyzing a blood cell, and more particularly, to a system for analyzing a blood cell, which analyzes the blood cells included in blood to classify the blood cells by kind by using the analysis result, and a method thereof.

2. Description of the Related Art

An in-vitro diagnostic device, which is equipment capable of diagnosing disease from an outside of a human body, is able to perform examination based on a substance, such as blood, saliva, etc., generated from a human body.

A complete blood cell (CBC), which gives information about red blood cells, white blood cells and platelets existing in blood, is one of the most basic blood examinations among examination schemes using in-vitro diagnostic device, which has various clinical indications including diagnosis, treatment and tracking observation of disease.

The general blood examination may obtain the information about cells (corpuscles) of three kinds, that is, red blood cells, white blood cells and platelets by using various parameters.

For the general blood examination, an automatic blood cell analyzer for automatically measure the number of blood cells in a volume to obtain information about the number of blood cells after suitably diluting blood has been widely used.

Since the automatic blood cell analyzer can measure various parameters as well as the count information, the automatic blood cell analyzer has been widely used rather than a counting scheme of measuring the number of cells through a microscope by using a hemocytometer.

In recent years, a flow cytometer and flow cytometry, which can simultaneously measure several information about a cell, such as a size of a cell, a cell inner composition, cell function recognition, etc., by using the light scattering caused by exposing the cell to laser while allowing the cell to pass through a narrow tube and the light emission of a fluorescent material and can sort out a specific cell, have been widely used.

There has been disclosed a technique about an apparatus for sorting a fluorescent activation biology cell and a cell sorting method in following patent document 1 (Korean Patent Registered No. 10-0619256 issued on Aug. 31, 2006).

As disclosed in patent document 1, according to a cell sorting method of the related art, a laser beam is emitted to a cell by using a laser source such as a laser diode such that light is scattered while passing through the cell, and a distribution of scattered light is detected by using light-scattering effect, thereby sorting cells according to the detected scattered light.

For example, FIG. 1 is a view illustrating the configuration of a cell analyzing apparatus according to the related art.

As shown in FIG. 1, according to a cell analyzing apparatus of the related art, a laser beam is irradiated from a laser 1 toward a path along which a target cell moves. A plurality of photodetectors 2 are installed to a portion to which the irradiated laser beam passes through the target cell, such that the light density of the light path formed around the target cell according to an angle is measured. Then, kinds of the cells are sorted by using a cell identifying analysis result.

Such a cell analyzing apparatus includes a collimating lens 3 for collimating a laser beam irradiated from a laser, a first focusing lens 4 allowing the laser beam to be irradiated onto a cell to be analyzed by focusing a section of the collimated laser beam in a spot shape, and a second focusing lens 5 for focusing a laser beam generated as a result of refraction, reflection, transmission or fluorescence of the laser beam incident upon a blood cell and transferring the focused laser beam to a photodetector.

However, according to the cell analyzing apparatus of the related art, a space is required to install lenses such as the collimating lens 3, the first and second lenses 4 and 5, and the like and a complex lens designing process is required, so that the configuration of the cell analyzing apparatus is complex. Thus, the manufacturing workability deteriorates and the manufacturing cost is increased.

Meanwhile, in the process of sorting a cell, when a cell moves along a path on which a laser beam is irradiated to a classifying target cell, the distribution of elements of the cell may be changed as the cell is rotated.

For this reason, since the laser is irradiated at one side of the moving path, the densities of light detected at each angle by the photodetector are different from each other, so the cell analyzing apparatus according to the related art cannot exactly analyze the cell.

In addition, since the cell analyzing apparatus according to the related art uses a single laser beam, the cell analyzing apparatus cannot correctly analyze and classify blood cells which are identified as mutually different cells in spite of having the same shape.

SUMMARY OF THE INVENTION

To solve the problems described above, one object of the present invention is to provide an apparatus for analyzing a blood cell of which the structure is simplified and miniaturized by removing lenses for focusing a laser beam, and an analysis method thereof.

Another object of the present invention is to provide an apparatus for analyzing a blood cell, which is capable of improving the accuracy of a blood cell analysis result by allowing one light source to display effect corresponding to that obtained through plural light sources, and an analysis method thereof.

Still another object of the present invention is to provide an apparatus for analyzing a blood cell, which is capable of analyzing a blood cell using plural light sources configured to irradiate laser beams having mutually different colors, and an analysis method thereof.

To achieve the objects described above, according to one aspect of the present invention, there is provided a system for analyzing a blood cell, which includes: a laser generator installed around a moving path, along which an analysis target blood cell moves, to generate a laser beam; a plurality of photodetectors configured to detect a laser beam generated as a result of refraction, reflection, transmission or fluorescence of the laser beam generated from the laser generator and incident upon the analysis target blood cell; and an optical fiber configured to focus the laser beam generated from the laser generator and to irradiate the focused laser beam to a measurement point existing on the moving path, wherein the optical fiber transfers a laser beam scattered through a blood cell to the photodetectors; and an analysis apparatus configured to analyze the analysis target blood cell by using the laser beam detected by the photodetectors.

According to another aspect of the present invention, there is provided a method of analyzing a blood cell, which includes the steps of: (a) irradiating a laser beam to a measurement point existing on a moving path of an analysis target blood cell by using a laser generator; (b) focusing the laser beam generated from the laser generator by using an optical fiber to irradiate the focused laser beam to the measurement point; (c) focusing a laser beam generated as a result of refraction, reflection, transmission or fluorescence of the laser beam incident upon the analysis target blood cell, wherein the focused laser beam is transferred to a photodetector to be detected, and (d) analyzing the analysis target blood cell based on the detected laser beam by the photodetector in an analysis apparatus.

As described above, according to the system and the method for analyzing a blood cell of the present invention, the laser beam generated from the laser generator is focused through the optical fiber and is irradiated to a blood cell. Then, the laser beam scattered through the blood cell is focused and is transferred to the photodetector, so that the blood cell may be precisely analyzed.

That is, according to the present invention, the lens applied to a cell analysis apparatus according to the related art is omitted and the laser beam focused through the optical fiber is irradiated to a blood cell for the purpose of analysis, so that the process of designing a space for installing a lens therein and a complex lens may be omitted, thereby miniaturizing the system for analyzing a blood cell and simplifying the structure of the system.

In addition, according to the present invention, the laser beam having an elliptical-shaped section is irradiated to a blood cell through the optical fiber in order to analyze the blood cell, such that the blood cells, which overlap each other while simultaneously moving in the flow cell 12, may be analyzed and classified.

In addition, according to the present invention, one end of the optical fiber is branched into a plurality of optical fibers to irradiate the laser beam to the blood cell at mutually different angles through the branched optical fibers and the distribution of the laser beams which are refracted and reflected from the blood cell and transmit through the blood cell can be found so that the blood cell may be classified based on the laser beam distribution.

In detail, according to the present invention, by irradiating the laser beams at mutually different angles or with mutually different frequencies in case of a co-axial direction through the branched rear end of the optical fiber and by using two or three-dimensional distribution of laser beams scattered by the blood cells, the limitation of the laser beam distribution analysis due to the rotation of the blood cells may be minimized, so that the precision may be prevented from being deteriorated due to scattering variation and the blood cell may be exactly classified.

In addition, according to the present invention, since blood cells having similar shapes are exactly distinguished from each other through optical reactions of the blood cell to mutually different frequencies and the blood is very precisely grasped by grasping the distribution of the laser beams at various angles, the blood cells may be classified into very various kinds, for example, at least six kinds.

In addition, according to the present invention, a plurality of optical fibers are installed between the laser generators for generating laser beams having mutually different colors and the flow cell and between the flow cell and each photodetector to implement a plurality of beam paths, so that red and white blood cells may be analyzed by using the laser beams having mutually different colors.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, an apparatus and a method for analyzing a blood cell according to a preferable embodiment of the present invention will be described with reference to the accompanying drawings.

According to the present invention, a laser beam generated from a laser generator is focused and the focused laser beam is irradiated to a measuring point of a flow cell, such that the laser beam, which is generated as the result of refraction, reflection, transmission or fluorescence of the laser beam incident upon a blood cell, is detected to analyze a target blood cell.

Embodiment 1

Figure 1:
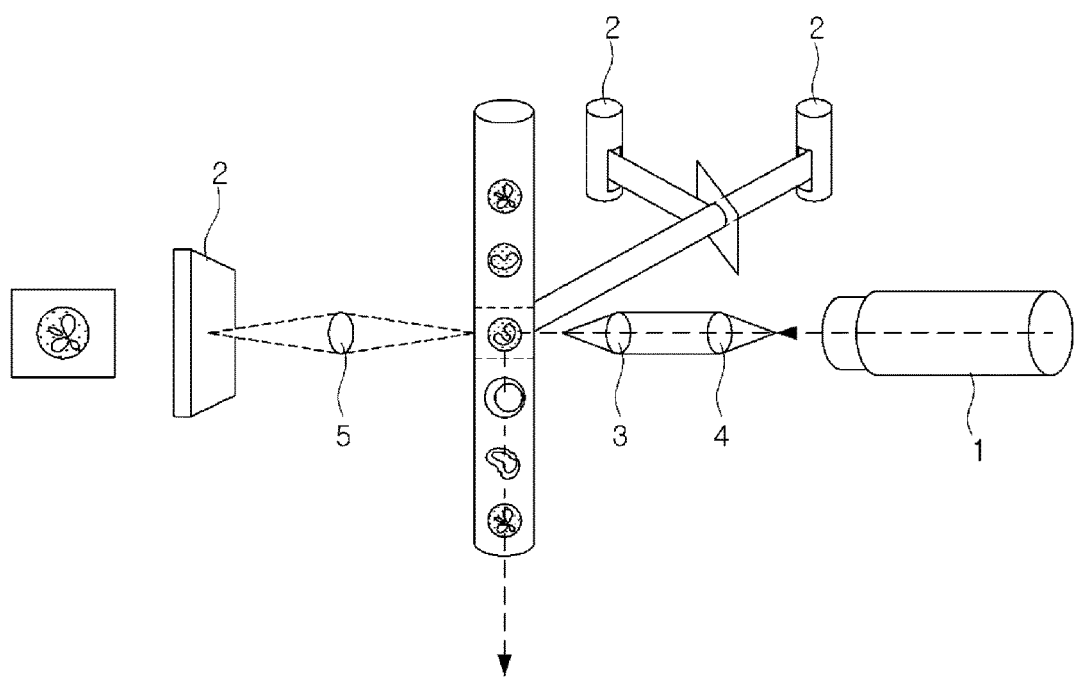
FIG. 1 is a view illustrating the configuration of a cell analyzing apparatus according to the related art.
Figure 2:
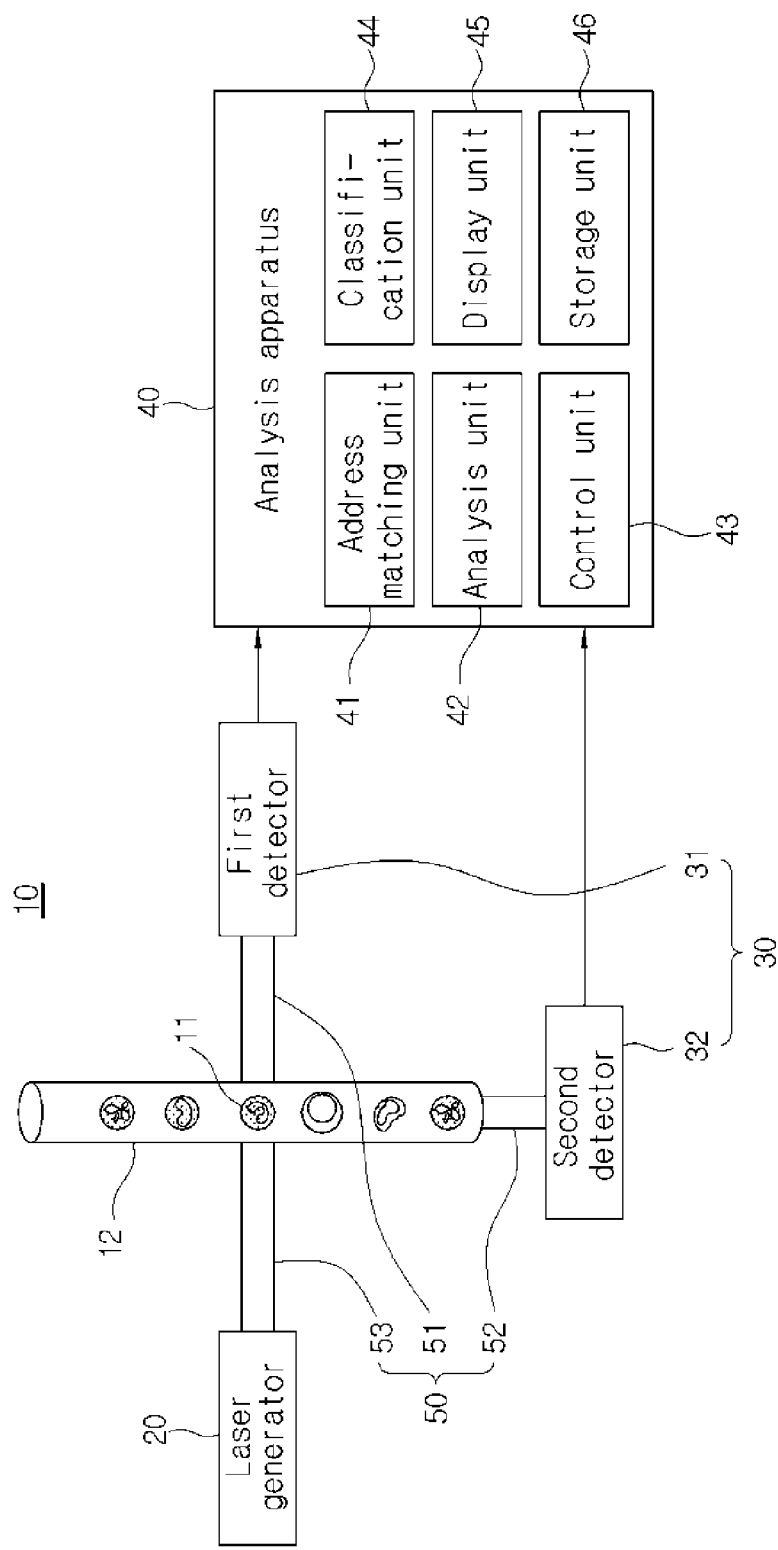
FIG. 2 is a view illustrating the configuration of a system for analyzing a blood cell according to a first embodiment of the present invention.

FIG. 2 is a view illustrating the configuration of a system for analyzing a blood cell according to a first embodiment of the present invention.

Referring to FIG. 2, a system 10 for analyzing a blood cell according to a first embodiment of the present invention includes a laser generator 20 installed around a moving path along which an analysis target blood cell moves to generate a laser beam, a plurality of photodetectors 30 configured to detect a laser beam generated as a result of refraction, reflection, transmission or fluorescence of the laser beam incident upon the analysis target blood cell, and an analysis apparatus 40 configured to analyze the analysis target blood cell by using the laser beam detected by the photodetectors 30.

In particularly, the system for analyzing a blood cell according to the first embodiment of the present invention further includes an optical fiber 50 configured to focus the laser beam generated from the laser generator 20 and to irradiate the focused laser beam to a measurement point 11 existing on the moving path. In addition, the optical fiber 50 transfers a laser beam scattered through a blood cell to the photodetectors 30.

As shown in FIG. 2, the analysis target blood cell (hereinafter, referred to as a "blood cell") is mixed with a sheath liquid in a chamber (not shown) provided on an upper end of the flow cell 12 and moves along a moving path formed in the flow cell 12.

One measurement point 11 to which the laser beam is irradiated may be set on the moving path.

The laser generator 20 is installed around the moving path along which the blood cell moves and irradiates the laser beam to the measurement point 11 on the moving path.

The laser beams irradiated from the laser generator 20 have mutually different natural frequencies. Even though the laser beams having mutually different natural frequencies are focused on the measurement point 11, the laser beams do not interfere with each other due to the characteristics of a laser beam.

The photodetector 30 may include a first detector 31 configured to detect a laser beam which is forward-scattered while passing through the blood cell moving through the moving path, and a second detector 32 configured to detect a laser beam which is refracted, reflected or fluorescent from the blood cell to be side-scattered toward a side surface of the blood cell.

The first detector 31 may be installed to be symmetrical to the laser generator 20 with respect to the measurement point 11. The second detector 32 may be installed to be angled to the laser generator 20 at about 90°.

Of course, the second detector 32 may be installed to be angled at various angles according to a blood cell analysis result and a kind of target blood cell.

Thus, the laser beam detected by the first detector 31 may be used to measure a size of each blood cell (normal and abnormal blood cells), and the laser beam detected by the second detector 32 may be used to measure fluorescence, granularity and internal complexity of each blood cell.

Of course, the installation angle between the laser generator 20 and the photodetector 30 may be variously changed based on the results of blood analysis performance examinations performed at various angles.

Hereinafter, a configuration of the optical fiber will be described in detail with reference to FIG. 3.

Figure 3:
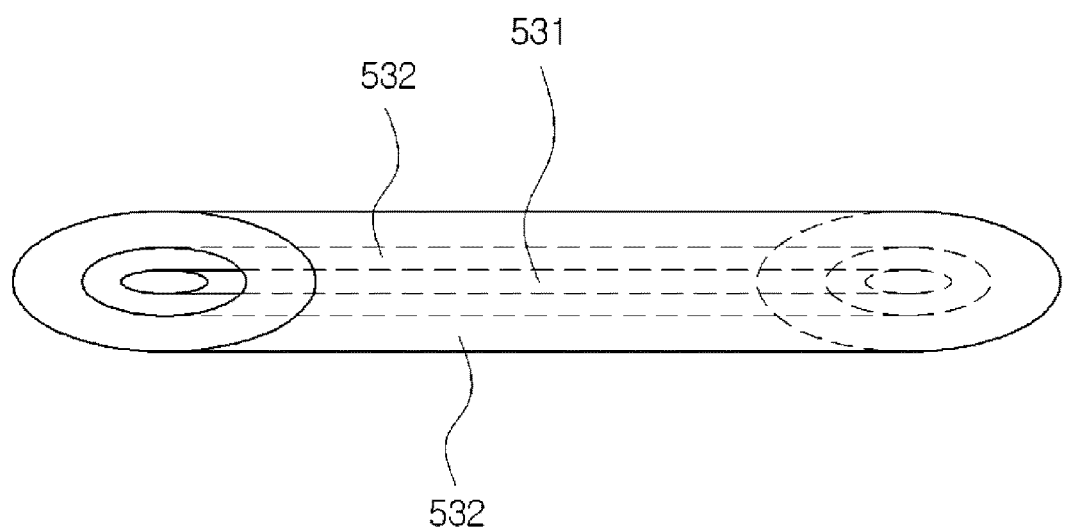
FIG. 3 is a perspective view of a third optical fiber depicted in FIG. 2.

FIG. 3 is a perspective view of a third optical fiber depicted in FIG. 2.

Instead of the lenses of a cell analysis apparatus according to the related art, the optical fiber 50 allows the laser beam generated from the laser generator 20 to be irradiated to the blood cell while the laser beam is focused. The optical fiber 50 focuses the laser beam scattered through the blood cell to transfers the focused laser beam to the photodetector 30.

That is, the optical fiber 50 may include a first optical fiber 51 configured to focus the laser beam forward-scattered through the blood cell and transfer the focused laser beam to the first detector 32, a second optical fiber 52 configured to focus the laser beam side-scattered through the blood cell and to transfer the focused laser beam to the second detector 32, and a third optical fiber 53 configured to focus the laser beam generated from the laser generator 20 and to irradiate the focused laser beam to the measurement point 11.

In this case, if necessary, the third optical fiber 53 may be removed and replaced with a lens.

Next, the configurations of the first to third optical fibers will be described in detail with reference to FIG. 3.

As shown in FIG. 3, the third optical fiber 532 may include a core 531 through which the laser beam passes and a clad 532 prepared at an outside of the core 531.

In addition, the third optical fiber 53 may further include a covered layer 533 covering an outer surface of the clad 532.

In the third optical fiber 53, a refractive index of the core 53 through which the beam passes may be less than that of the clad serving as a blocking layer for preventing light from radiating to an outside, so that the laser beam incident upon the core 531 is transmitted while being repeatedly total-reflected on the interface between the core 531 and the clad 532 having mutually different refractive indexes.

Specifically, the third optical fiber 53 may allow the laser beam having an elliptical-shaped section to be irradiated to the blood cell, such that the blood cells, which overlap each other while simultaneously moving in the flow cell 12, are analyzed and classified.

To this end, the core 531 and the clad 532 of the third optical fiber 53 may be formed to have elliptical-shaped sections by pressing the core 531 and the clad 532 from both sides of them after the core 531 and the clad 532 are fabricated to have circular-shaped sections.

Alternatively, the third optical fiber 53 may be fabricated to allow the core 531 and the clad 532 to have elliptical-shaped sections by forming the core 531 and the clad 532 in an elliptical shape.

Meanwhile, differently from the third optical fiber 53 having an elliptical-shaped section, the first and second optical fibers 51 and 52 may be fabricated to have circular-shaped sections.

Thus, according to the present invention, the lenses are omitted differently from a cell analysis apparatus according to the related art. The laser beam focused by using the optical fiber is irradiated to a blood cell and the laser beam scattered through the blood cell is transferred to the photodetector such that the blood cell may be analyzed.

Therefore, according to the present invention, the process of designing a space for installing a lens therein and a complex lens may be omitted, so that the system for analyzing a blood cell is miniaturized and the structure is simplified, thereby improving the fabrication workability and reducing the fabrication cost.

In addition, according to the present invention, the third optical fiber for irradiating a laser beam to a blood cell may be fabricated to have an elliptical-shaped section such that a laser beam having an elliptical shape is irradiated to a blood cell, thereby improving the precision of the result of analyzing a blood cell.

Referring to FIG. 2 again, the analysis apparatus 40 analyzes a blood cell using blood cell information detected by the photodetector 30 and classifies each blood cell.

To this end, the analysis apparatus 40 may include an address matching unit 41 configured to receive signals output from the first and second detectors 31 and 32 of the photodetector 30 and to match blood cell addresses included in the received signals, an analysis unit 42 configured to analyze a blood cell by using the operating result of the address matching unit 41, and a control unit 43 configured to control each unit included in the analysis apparatus 40.

In addition, the analysis apparatus 40 may further include a classifying unit 44 configured to classify all blood cells by kind based on the analysis result of each blood cell or to classify all blood cells according to classification criteria, and a display unit 45 configured to display information about a blood cell in order to provide an administrator with the analysis result of the analysis unit 42 and information about whether the blood cell is normal or abnormal.

The address matching unit 41 matches blood cell information detected by the first and second detectors 31 and 32 with a blood cell address assigned to the corresponding blood cell.

The analysis unit 42 may finally analyze blood cell information about a size of a blood cell, a shape, fluorescence and granularity and may determine whether the corresponding blood cell is normal or abnormal.

The control unit 43 may store the analysis result of the analysis unit 42 in a storage unit 46 and may distinguish a normal blood cell having a normal shape and an abnormal blood cell different from the normal blood cell from each other based on the stored analysis result. The control unit 43 may control the operation of the display unit 45 to provide information about the normal blood cell and the abnormal blood cell to an administrator.

Specifically, the control unit 43 may control the laser generator 20 such that the laser generator 20 generates and irradiates laser beams having the same frequency or mutually different frequencies.

Therefore, the laser generator 20 may irradiates laser beams having the same frequency or mutually different frequencies according to a control signal of the control unit 43.

The storage unit 46 may store standard blood cell information that is obtained by standardizing information about all analysis target blood cells.

The standard blood cell information may include information about a size, a shape, fluorescence or granularity of each blood cell.

Figure 4:
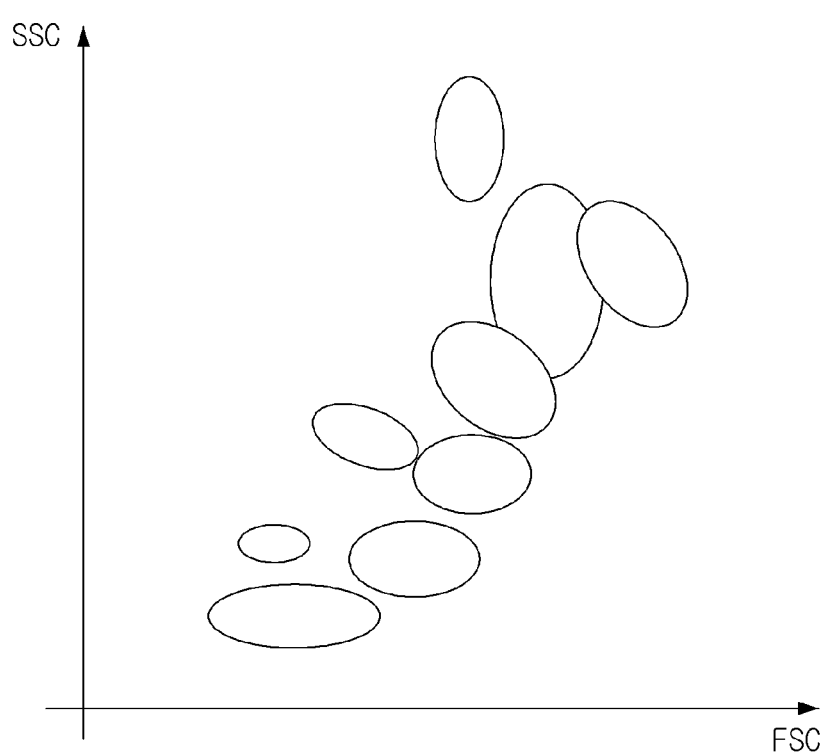
FIG. 4 is a view illustrating standard blood cell information.

For example, FIG. 4 is a view illustrating the standard blood cell information.

As shown in FIG. 4, the storage unit 46 may store the standard blood cell information in FSC/SSC dot plot.

The control unit 43 may compare the analysis result of the analysis unit 42 with the standard blood cell information stored in the storage unit 46. The control unit 43 may control the classification unit 44 such that the blood cells analyzed according to the comparison result are classified into several kinds, for example, six kinds or more, at most 14 kinds or 15 kinds.

Meanwhile, the analysis unit 42 may calculate beam quantities of laser beams by frequency based on the information about beam quantities and frequencies of laser beams, which is detected by the detectors 31 and 32, respectively. The analysis unit 42 may calculate information about three-dimensional laser beam distribution based on the information about beam quantities and frequencies of laser beams, and compare the information about three-dimensional laser beam distribution with the standard blood cell information.

As described above, the lens applied to a cell analysis apparatus according to the related art is omitted and the laser beam focused through the optical fiber is irradiated to a blood cell for the purpose of analysis, so that the process of designing a space for installing a lens therein and a complex lens may be omitted, thereby miniaturizing the system for analyzing a blood cell and simplifying the structure.

Next, an analysis method of the system for analyzing a blood cell according to the first embodiment of the present invention will be described in detail with reference to FIG. 5.

Figure 5:
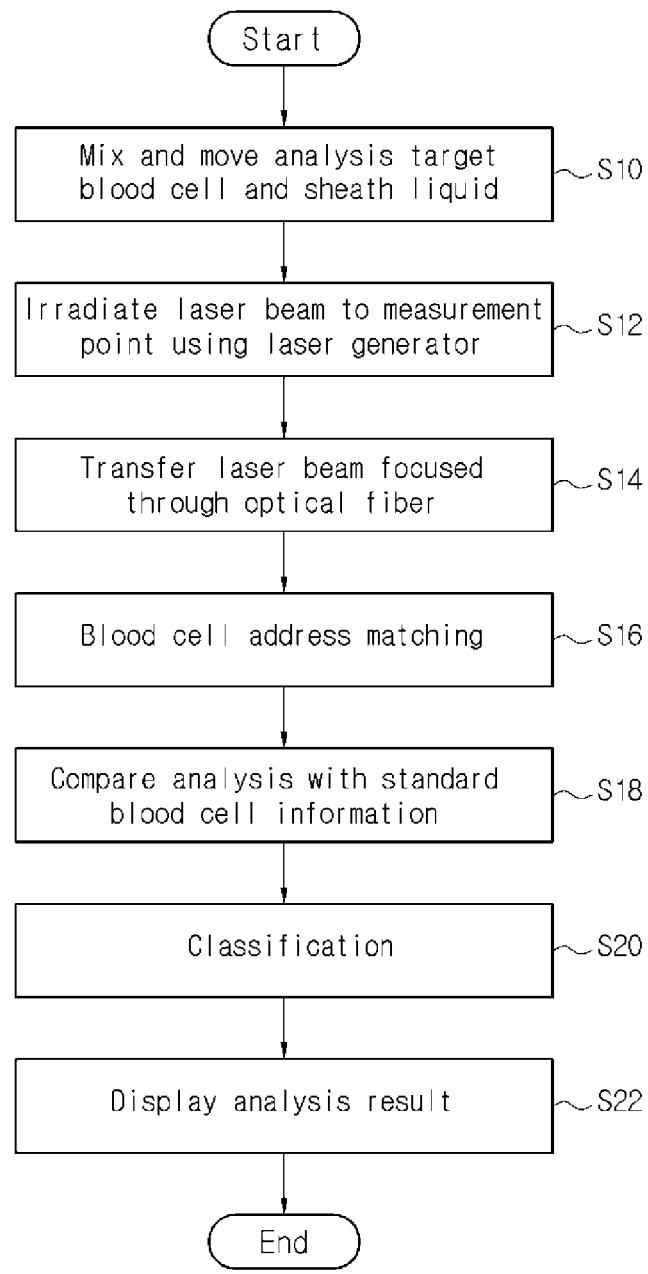
FIG. 5 is a flowchart illustrating an analysis method of the system for analyzing a blood cell according to the first embodiment of the present invention.

FIG. 5 is a flowchart illustrating an analysis method of the system for analyzing a blood cell according to the first embodiment of the present invention.

Referring to FIG. 5, in step S10, the analysis target blood cell moves along the moving path formed in the flow cell 12 after being mixed with the sheath liquid in the chamber.

In step S12, the laser generator 20 installed near the moving path irradiates the laser beam to the measurement point 11 on the moving path.

In step S14, third optical fiber installed between the laser generator 20 and the blood cell focuses the laser beam to allow the laser beam to have an elliptical-shaped section and irradiates the focused laser beam to the blood cell.

Thus, the first and second detectors 31 and 32 of the photodetector 30 detect the laser beam which passes through the blood cell to be forward-scattered and the laser beam which is refracted, reflected or fluorescent from the blood cell to be side-scattered toward the side surface of the blood cell.

In step S16, the address matching unit 41 provided to the analysis apparatus 40 matches the information about the blood cells detected by the first and second detectors 31 and 32, for example, with the blood addresses assigned to the blood cells.

In step S18, the analysis unit 42 analyzes information about each blood cell, such as a size, a shape, fluorescence or granularity of each blood cell so that a normal blood cell may be distinguished from an abnormal blood cell (ABN).

In step S20, the control unit 43 compares the analysis result with the standard blood cell information stored in the storage unit to finally sort the blood cells by kind. In addition, the control unit 43 may control the classification unit 44 such that all blood cells are classified by kind according to the classification result or according to a preset classification reference.

In step S22, the control unit 43 stores the analysis result of the analysis unit 2 in the storage unit 46 and may distinguish a normal blood cell having a normal shape and an abnormal blood cell different from the normal blood cell from each other based on the stored analysis result. The control unit 43 may control the operation of the display unit 45 to provide information about each blood cell to an administrator.

As described above, according to the present invention, the optical fibers are installed between the laser generator and the blood cell and the focused laser beam is irradiated to the blood cell. In addition, the blood cell moving along the moving path may be analyzed through the photodetector, so that the precision of the result of analyzing a blood cell may be improved.

In addition, according to the present invention, the precision of the result of analyzing a blood cell may be prevented from being deteriorated due to the movement and rotation of the blood cell on the moving path and scattering modification, so that the reliability is improved.

Meanwhile, although it has been described in the present embodiment to analyze a blood cell by using one laser generator and an optical fiber, the present invention is not limited thereto.

As one example of modifying the present invention, one optical fiber branches off to a plurality of optical fibers such that the laser beam generated from one laser generator may be irradiated to a blood cell at mutually different angles.

Embodiment 2

Figure 6:
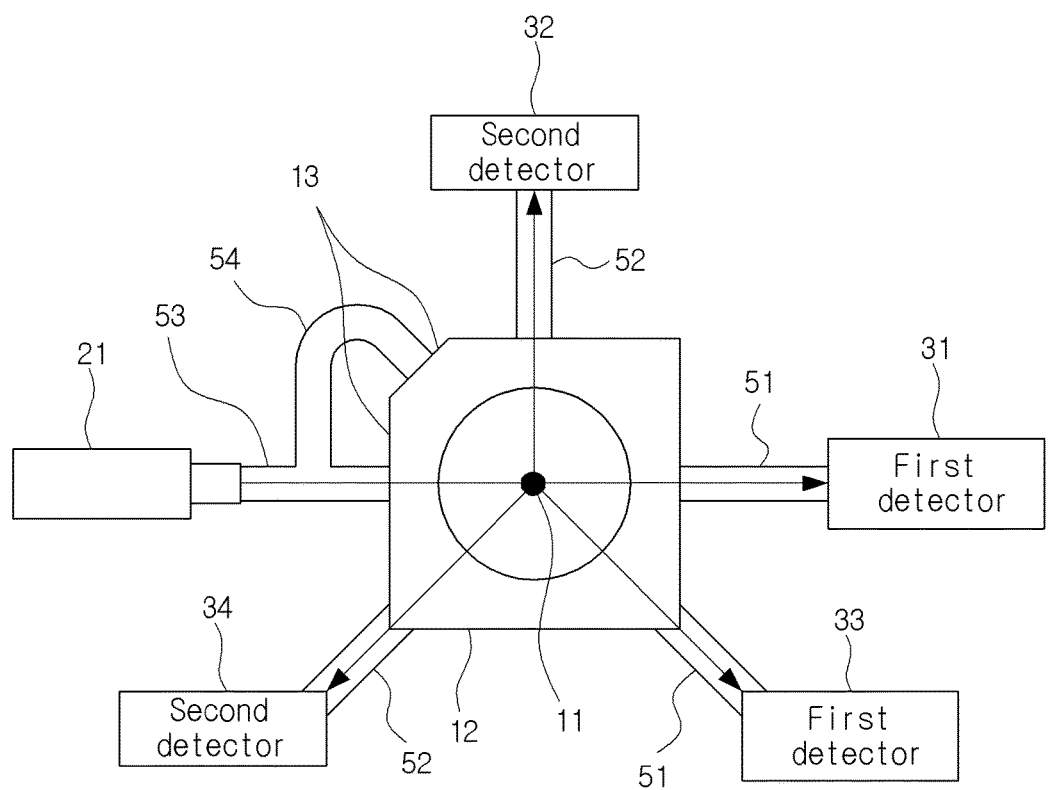
FIG. 6 is a view illustrating the configuration of a system for analyzing a blood cell according to a second embodiment of the present invention.

FIG. 6 is a view illustrating the configuration of a system for analyzing a blood cell according to a second embodiment of the present invention.

As shown in FIG. 6, the system 10 for analyzing a blood cell according to the second embodiment of the present invention has a configuration similar to that described with reference to FIG. 2. However, according to the system 10, a rear end of the third optical fiber 53 is branched into plural optical fibers so that the laser beams may be irradiated to the blood cell at mutually different angles.

To this end, an front end of the third optical fiber 53 may be connected to the laser generator 21 and a rear end of the third optical fiber 53 may be connected to at least one fourth optical fiber 54 branched from the third optical fiber 53.

A rear end of the fourth optical fiber 54 may be spaced apart from a rear end of the third optical fiber 53 around the measurement point 11 by a preset angle.

For example, the preset angle may be in the range of about 10° to about 170°.

The photodetector 30 may include a first detector 31 configured to detect a laser beam which is forward-scattered while passing through the blood cell moving through the moving path, a second detector 32 configured to detect a laser beam which is refracted, reflected or fluorescent from the blood cell to be side-scattered toward a side surface of the blood cell.

In addition, a plurality of first optical fibers 51 may be installed between a blood cell and a plurality of first detectors 31 and 33, and a plurality of second optical fibers 52 may be installed between the blood cell and a plurality of second detectors 32 and 34, respectively.

At least one measurement point 11 may be set on the moving path of a flow cell 12.

That is, one measurement point 11 may be set or a plurality of measurement points 11 may be set to be spaced apart from each other by a preset interval.

Thus, when laser beams are irradiated to the measurement points 11, the address matching unit 41 may synchronize times of the photodetectors 30 with each other and may match blood cell information with each other in consideration of delay times of the photodetectors 30.

In addition, as shown in FIG. 6, an inner section of the flow cell 12 may have a circular shape and an outer section of the flow cell 12 may have a rectangular shape.

When a plurality of laser generators 20 spaced apart from each other by a predetermined angle are installed around the flow cell 12 having an outer section of a rectangular shape to irradiate laser beams, the laser beams incident upon the outer surface of the flow cell 12 may be reflected, refracted or scattered according to angles to the outer surface of the flow cell 12, so that the quantity of the laser beams transferred to the blood cell may be reduced.

For this reason, the blood cell analysis performance and precision of the system 10 for analyzing a blood cell may be deteriorated.

To solve the problem, as shown in FIG. 6, an incident surface 13 orthogonal to the laser beams may be provided on the outer surface of the flow cell 12.

That is, the flow cell 12 may have an outer section having a polygonal shape and orthogonal to the laser beam incident upon the optical fibers 53 and 54.

Thus, the laser beams irradiated through the optical fibers 53 and 54 transmit the incident surfaces 13 formed on the flow cell 12 and are transferred to the moving path formed in the flow cell 12.

Thus, according to the present invention, the laser beams may be prevented from being reflected, refracted or scattered while being incident upon the flow cell, so that the quantity of laser beams transferred to the blood cell is kept at maximum.

Of course, the present invention is not necessarily limited to the above. The installing angle of each optical fiber may be changed to change the scattering distribution of the laser beams detected by the photodetector without regard to the quantity of laser beams transferred to the blood cell.

Therefore, according to the present invention, one end of the optical fiber is branched into a plurality of optical fibers to irradiate the laser beam to the blood cell at mutually different angles through the branched optical fibers and the distribution of the laser beams which are refracted and reflected from the blood cell and transmit through the blood cell is grasped such that the blood cell may be classified.

That is, when the blood cell is analyzed by irradiating the laser beams in a uni-direction, the blood cell may be rotated on the moving path and the distribution of elements of the blood cell may be changed due to the scattering modification of the laser beams. Thus, even in case of the same blood cell, the density of the laser beam detected at each angle by the photodetector, that is, the distribution of the laser beams may be changed.

Thus, when the blood cell is analyzed by irradiating only uni-directional laser beams according to the related art, very limited kinds of blood cells may be only classified due to the simplicity of the uni-direction.

In addition, although there is a difference even between blood cells having mutually similar shapes in elements constituting the blood cells, in case of the analysis through laser beams having a single frequency, mutually different cells cannot be distinguished from each other.

However, according to the present invention, by irradiating the laser beams at mutually different angles or with mutually different frequencies in case of a co-axial direction through the branched rear end of the optical fiber and using two or three-dimensional distribution of laser beams scattered by the blood cells, the limitation of the laser be distribution analysis due to the rotation of the blood cells may be minimized, so that the precision may be prevented from being deteriorated due to scattering modification and the blood cell may be exactly classified In addition, according to the present invention, since blood cells having similar shapes are exactly distinguished from each other through optical reactions of the blood cell to mutually different frequencies and the blood is very precisely grasped by grasping the distribution of the laser beams at various angles, the blood cells may be classified into very various kinds, for example, at least six kinds.

In the above embodiments, although it is described to analyze a blood cell by using one laser generator, the present invention may be modified to analyze a blood cell by applying a plurality of laser generators irradiating laser beams having mutually different colors.

Embodiment 3

In general, when red and white blood cells are analyzed, laser beams having mutually different colors such as red and blue is irradiated to analyze each blood cell.

Thus, a plurality of laser generators for outputting laser beams having mutually different colors may be prepared to irradiate the laser beams having mutually different colors generated from the laser generators through a plurality of optical fibers.

Figure 7:
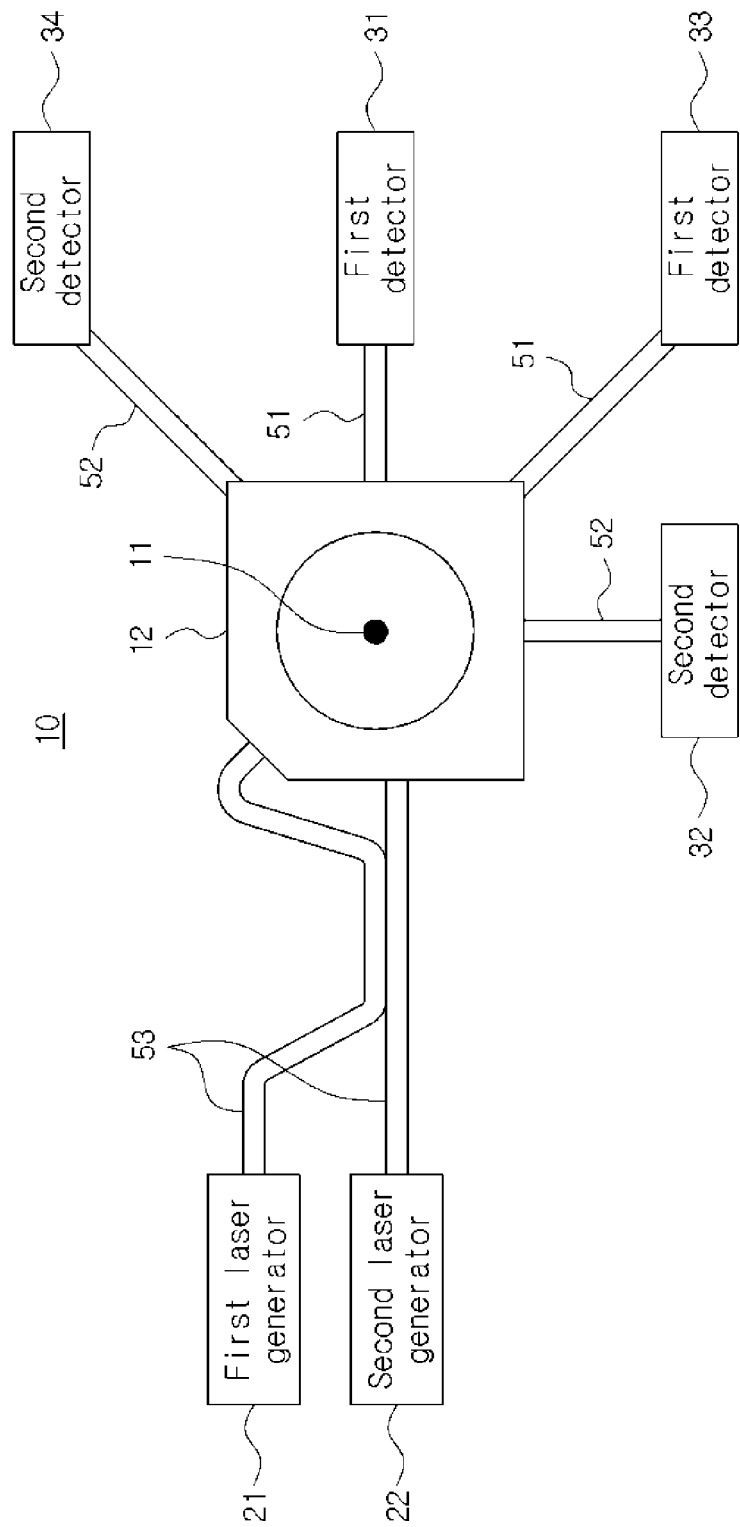
FIG. 7 is a view illustrating the configuration of a system for analyzing a blood cell according to a third embodiment of the present invention.

FIG. 7 is a view illustrating the configuration of a system for analyzing a blood cell according to a third embodiment of the present invention.

As shown in FIG. 7, the system 10 for analyzing a blood cell according to the third embodiment of the present invention has a configuration similar to that described with reference to FIG. 6. However, according to the system 10, a plurality of third optical fibers 53 may be prepared to irradiate laser beams having mutually different colors at mutually different angles.

To this end, the laser generator 20 may include first and second laser generators 21 and 22 configured to generate laser beams having mutually different colors, for example, red and blue, and a plurality of third optical fibers 53 may be installed between the first and second laser generators 21 and 22 and a blood cell.

In addition, a plurality of first optical fibers 51 may be installed between the blood cell and a plurality of first detectors 31 and 33 and a plurality of second optical fibers may be installed between the blood and a plurality of second detectors 32 and 34, respectively.

Front ends of each of a plurality of third optical fibers 53 may be connected to the first and second laser generators 21 and 22, respectively, and rear ends of the third optical fibers 53 may be installed near the flow cell 12 to be orientated to the blood cell while being spaced apart from each other by a preset angle to the measurement point 11.

In this case, central parts of the third optical fibers 53 may be combined with each other to be installed in one bundle.

As described above, according to the present invention, the optical fibers are installed between the laser generators for generating laser beams having mutually different colors and the flow cell to implement a plurality of beam paths while being spaced apart from each other by a preset angle, so that red and white blood cells may be analyzed by using the laser beams having mutually different colors.

According to the process described above, the laser beam generated from the laser generator is focused through the optical fiber and is irradiated to a blood cell. Then, the laser beam scattered through the blood cell is focused and is transferred to the photodetector, so that the blood cell may be precisely analyzed.

Although an exemplary embodiment of the present invention has been described for illustrative purposes, those skilled in the art will appreciate that various modifications, additions and substitutions are possible, without departing from the scope and spirit of the invention as disclosed in the accompanying claims.

The present invention may be applied to a technique of analyzing a blood cell, in which the laser beam generated from the laser generator is focused and is irradiated to a blood cell, and the laser beam scattered through the blood cell is focused and is transferred to the photodetector such that the blood cell is precisely analyzed.

What is claimed is:

1. A system for analyzing a blood cell, the system comprising:
   a laser generator generating a laser beam and a first, a second and a third optical fibers,
   wherein the third optical fiber comprises a fourth optical fiber branched therefrom and having a rear end;
   wherein a front end of the third optical fiber is connected to the laser generator, a rear end of the third optical fiber is configured to focus the laser beam generated from the laser generator and to irradiate a measurement point existing on a moving path, along which an analysis target blood cell moves, with the focused laser beam;
   wherein said rear end of the fourth optical fiber is spaced apart from the rear end of the third optical fiber by a preset angle based on the measurement point, and configured to focus the laser beam generated from the laser generator and irradiate the measurement point existing on said moving path, along which the analysis target blood cell moves, with the focused laser beam of the fourth optical fiber; and
   wherein the first and second optical fibers each are configured to transfer a laser beam scattered through the analysis target blood cell to a plurality of photodetectors configured to detect the scattered laser beam scattered as a result of refraction, reflection, transmission or fluorescence of the laser beam generated from the laser generator and incident upon the analysis target blood cell; and
   an analysis apparatus configured to analyze the analysis target blood cell by using the laser beam detected by the plurality of photodetectors,
   wherein the first optical fiber is configured to focus a laser beam forward-scattered through the analysis target blood cell and to transfer the focused, forward-scattered laser beam to a first photodetector of the plurality of photodetectors, and
   wherein the second optical fiber is configured to focus a laser beam side-scattered through the analysis target blood cell and to transfer the focused side-scattered laser beam to a second detector of the plurality of photodetectors.

2. The system of claim 1,
   wherein each of the first, the second, and the third optical fibers comprises:
   a core through which a laser beam passes;
   a clad provided at an outside of the core; and
   a coated layer configured to cover an outer surface of the clad,
   wherein the core and the clad applied to each of the first, second and third optical fibers have an elliptical-shaped section such that a laser beam having an elliptical-shaped section is irradiated to the blood cell.

3. The system of claim 2, wherein the analysis apparatus comprises:
   an address matching unit configured to receive signals output from one or more of the plurality of photodetectors to match addresses of the blood cell included in the signals;
   an analysis unit configured to analyze the blood cell by using a processed result of the address matching unit;
   a control unit configured to control operations of each element provided to the analysis apparatus; and
   a classification unit configured to classify all blood cells according to the analysis result of each blood cell or according to a preset classification reference,
   wherein the control unit controls the classification unit to classify the blood cells analyzed according to a result of comparing the analysis result of the analysis unit and previously stored standard blood cell information, thereby classifying the analyzed blood cells.

4. The system of claim 1, wherein the plurality of photodetectors comprise:
   a plurality of first detectors configured to detect a laser beam which is irradiated through the third and the fourth optical fibers and passes through a blood cell moving along the moving path to be forward scattered; and
   a plurality of second detectors configured to detect a laser beam which is refracted, reflected or fluorescent from a blood cell to be side-scattered toward a side surface of the blood cell.

5. The system of claim 3, wherein the laser generator comprises a plurality of laser generators configured to generate laser beams having mutually different colors,
- the third optical fiber comprises a plurality of third optical fibers connected to the plurality of laser generators, respectively,
- central parts of the plurality of third optical fibers are combined with each other into one unit and installed in a bundle form, and
- rear ends of the third plurality of optical fibers are installed at mutually different angles around the measurement point and irradiate laser beams having the mutually different colors.

6. The system of claim 3, wherein the laser generator comprises a plurality of laser generators configured to generate laser beams having mutually different colors,
- the third optical fiber comprises a plurality of third optical fibers connected to the plurality of laser generators, respectively, and
- rear ends of the third plurality of optical fibers irradiate at least one measurement point with the laser beams having the mutually different colors, respectively.

7. A method of analyzing a blood cell, using a first, a second, and a third optical fibers, wherein the third optical fiber comprising a fourth optical fiber branched therefrom, the method comprising:
- (a) generating a laser beam by using a laser generator;
- (b) focusing the laser beam generated from the laser generator by using a rear end of the third optical fiber to irradiate a measurement point existing on a moving path of an analysis target blood cell with the focused laser beam, and focusing the laser beam generated from the laser beam by using a rear end of the fourth optical fiber to irradiate the measurement point with the focused laser beam of the fourth optical fiber, wherein a front end of the third optical fiber is connected to the laser generator, and wherein said rear end of the fourth optical fiber is spaced apart from the rear end of the third optical fiber by a preset angle based on the measurement point;
- (c) focusing a laser beam scattered as a result of refraction, reflection, transmission or fluorescence of the laser beam generated from the laser generator and incident upon the analysis target blood cell, wherein the scattered and focused laser beam is transferred to a plurality of photodetectors to be detected by the plurality of photodetectors, by using the first and the second optical fibers; and
- (d) analyzing the analysis target blood cell based on the detected laser beam by the plurality of photodetectors in an analysis apparatus,
- wherein the focusing of the scattered laser beam comprises:
  - (c1) focusing a laser beam forward-scattered through the analysis target blood cell and transferring the focused, forward-scattered laser beam to a first detector of the plurality of photodetectors by using the first optical fiber; and
  - (c2) focusing a laser beam side-scattered through the analysis target blood cell and transferring the focused, side-scattered laser beam to a second detector of the plurality of photodetectors by using the second optical fiber.

8. The method of claim 7, wherein the third optical fiber has an elliptical-shaped section such that a laser beam having an elliptical-shaped section is irradiated to the measurement point.

9. The method of claim 7, wherein the plurality of photodetectors includes a plurality of first photodetectors and a plurality of second photodetectors, and the first optical fiber has a plurality of first optical fibers and the second optical fiber has a plurality of second optical fibers;
- wherein the focusing of the forward-scattered laser beam comprises detecting a laser beam which is irradiated through the third and the fourth optical fiber and passes through a blood cell moving along the moving path to be forward scattered by using the plurality of first photodetectors connected to the plurality of first optical fibers installed to be symmetrical to the third and the fourth optical fibers with respect to the measurement point; and
- wherein the focusing of the side-scattered laser beam comprises detecting a laser beam which is refracted, reflected or fluorescent from the analysis target blood cell to be side-scattered toward a side surface of the analysis target blood cell by using the plurality of second photodetectors connected to the plurality of second optical fibers spaced apart from the third and the fourth optical fibers by a preset angle with respect to the measurement point.

10. The method of claim 8, wherein the laser generator has a plurality of laser generators and the third optical fiber has a plurality of third optical fibers,
- wherein the generating of the laser beam comprises generating laser beams having mutually different colors by using the plurality of laser generators, and
- wherein the focusing of the scattered laser beam further comprises irradiating the measurement point with the laser beams having the mutually different colors by installing the plurality of third optical fibers at mutually different angles around the measurement point, and wherein the plurality of third optical fibers are connected to the plurality of laser generators, respectively.

11. The method of claim 8, wherein the laser generator has a plurality of laser generators and the third optical fiber has a plurality of third optical fibers,
- wherein the generating of the laser beam comprises generating laser beams having mutually different colors by using the plurality of laser generators, and
- wherein the focusing of the scattered laser beam further comprises irradiating at least one measurement point with the laser beams having the mutually different colors by using the plurality of third optical fibers connected to the plurality of laser generators, respectively.

* * * * *